US012648707B2

(12) United States Patent
Mangual-Soto et al.

(10) Patent No.: US 12,648,707 B2
(45) Date of Patent: Jun. 9, 2026

(54) SYSTEM AND METHOD FOR DIFFERENTIATION OF ADIPOSE TISSUE FROM SCAR TISSUE DURING ELECTROPHYSIOLOGICAL MAPPING

(71) Applicant: St. Jude Medical, Cardiology Division, Inc., St. Paul, MN (US)

(72) Inventors: Jan O. Mangual-Soto, Rho (IT); Craig Markovitz, Mahtomedi, MN (US); Chunlan Jiang, N. Crystal, MN (US); Louis-Philippe Richer, Montreal (CA); Cyrille Casset, Saint-Selve (FR)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 717 days.

(21) Appl. No.: 15/907,512

(22) Filed: Feb. 28, 2018

(65) Prior Publication Data

US 2018/0249928 A1 Sep. 6, 2018

Related U.S. Application Data

(60) Provisional application No. 62/466,079, filed on Mar. 2, 2017.

(51) Int. Cl.
A61B 5/0537 (2021.01)
A61B 5/00 (2006.01)
(Continued)

(52) U.S. Cl.
CPC .......... A61B 5/0537 (2013.01); A61B 5/0538 (2013.01); A61B 5/24 (2021.01);
(Continued)

(58) Field of Classification Search
CPC ....... A61B 5/0537; A61B 5/6852; A61B 5/04; A61B 5/0422; A61B 5/6858;
(Continued)

(56) References Cited

U.S. PATENT DOCUMENTS

| | | | |
|---|---|---|---|
| 5,697,377 | A | 12/1997 | Wittkampf |
| 5,983,126 | A | 11/1999 | Wittkampf |
| | | (Continued) | |

FOREIGN PATENT DOCUMENTS

| | | |
|---|---|---|
| JP | 2008-523929 | 7/2008 |
| JP | 2008-536627 | 9/2008 |
| JP | 2015-528352 | 9/2015 |

OTHER PUBLICATIONS

Tung et al., Distinguishing Epicardial Fat from Scar: Analysis of Electrograms Using High Density Electroanatomic Mapping in a Novel Porcine Infarct Model, Heart Rhythm, Mar. 2010, 7(3): 389-395.

(Continued)

*Primary Examiner* — Tse W Chen
*Assistant Examiner* — Joseph A Tombers
(74) *Attorney, Agent, or Firm* — Wiley Rein LLP

(57) ABSTRACT

Methods, apparatuses, and systems to differentiate adipose tissue from scar tissue are disclosed. One or more electrophysiology data points, each of which includes an electrophysiological signal associated with a tissue location that possesses certain signal characteristics, can be collected. An adipose tissue probability and/or a scar tissue probability can be computed using the characteristics of the electrophysiological signal, such as signal duration, signal amplitude, signal fractionation, and/or late potentials. The probability computation can also utilize dielectric properties, such as tissue impedance, tissue conductivity, and/or tissue permittivity, measured at the tissue location. Graphical representations of the adipose tissue probability and/or scar tissue probability can also be output.

7 Claims, 7 Drawing Sheets

(51) Int. Cl.

| | |
|---|---|
| *A61B 5/0538* | (2021.01) |
| *A61B 5/24* | (2021.01) |
| *A61B 5/287* | (2021.01) |
| *A61B 34/10* | (2016.01) |

(52) U.S. Cl.

CPC ............ *A61B 5/287* (2021.01); *A61B 5/6852* (2013.01); *A61B 5/6858* (2013.01); *A61B 5/743* (2013.01); *A61B 34/10* (2016.02); *A61B 2034/105* (2016.02); *A61B 2034/107* (2016.02); *A61B 2562/0209* (2013.01); *A61B 2562/04* (2013.01); *A61B 2562/06* (2013.01)

(58) Field of Classification Search

CPC ....... A61B 5/0538; A61B 5/743; A61B 34/10; A61B 2562/06; A61B 2562/04; A61B 2034/105; A61B 2034/107; A61B 2562/0209

See application file for complete search history.

(56) References Cited

U.S. PATENT DOCUMENTS

| | | | |
|---|---|---|---|
| 6,640,119 | B1 | 10/2003 | Budd et al. |
| 6,728,562 | B1 | 4/2004 | Budd et al. |
| 6,939,309 | B1 | 9/2005 | Beatty et al. |
| 6,947,785 | B1 | 9/2005 | Beatty et al. |
| 6,978,168 | B2 | 12/2005 | Beatty et al. |
| 6,990,370 | B1 | 1/2006 | Beatty et al. |
| 7,263,397 | B2 | 8/2007 | Hauck et al. |
| 7,885,707 | B2 | 2/2011 | Hauck |
| 2001/0051774 | A1 | 12/2001 | Littrup et al. |
| 2006/0241708 | A1 | 10/2006 | Boute |
| 2009/0099468 | A1 | 4/2009 | Thiagalingam et al. |
| 2011/0264000 | A1* | 10/2011 | Paul ..................... A61B 5/0537 600/547 |
| 2013/0072774 | A1 | 3/2013 | Greenspan |

OTHER PUBLICATIONS

International Search Report and Written Opinion issued in the corresponding PCT application (PCT/US2018/020116); mailed on Jun. 5, 2018 (Jun. 5, 2018).

International Preliminary Report on Patentability Chapter I issued in the corresponding PCT application (PCT/US2018/020116); mailed on Sep. 3, 2019 (Sep. 3, 2019).

Takeshi Sasaki et al: "Impact of Scar, Viable Myocardium, and Epicardial Fat on Substrate Identification of Ventricular Tachycardia in a Case with Nonischemic Cardiomyopathy : Effect of Scar and Fat On Voltage Mapping in Nonischemic Cardiomyopathy" , PACE—Pacing and Clinical Electrophysiology., vol. 35, No. 12, Sep. 2, 2011 (Sep. 2, 2011), pp. e345-e348.

Benoit Desjardins et al: "Effect of Epicardial Fat on Electroanatomical Mapping and Epicardial Catheter Ablation", Journal of the American College of Cardiology, vol. 56, No. 16, Oct. 1, 2010 (Oct. 1, 2010), pp. 1320-1327.

University of Pennsylvania: "Measuring Electrical Resistance of Different Tissues on the Outer Surface of the Heart" Aug. 16, 2016 (Aug. 16, 2016), Retrieved from the Internet: URL: https://clinicaltrials.gov/ct2/show/NCT00291174 retreived.

Sanjay Dixit et al: "Electroanatomic Mapping of Human Heart:", Journal of Cardiovascular Electrophysiology., vol. 14, No. 10, Oct. 1, 2003 (Oct. 1, 2003), pp. 1128-1128.

Gerard Amoros-Figueras et al: "Recognition of Fibrotic Infarct Density by the Pattern of Local Systolic-Diastolic Myocardial Electrical Impedance", Frontiers in Physiology, vol. 7, Aug. 31, 2016 (Aug. 31, 2016).

M.K Konings et al: "Development of an intravascular impedance catheter for detection of fatty lesions in arteries", IEEE Transactions on Medical Imaging, Jan. 1, 1997 (Jan. 1, 1997), pp. 439-446.

* cited by examiner

FIG.5

SYSTEM AND METHOD FOR DIFFERENTIATION OF ADIPOSE TISSUE FROM SCAR TISSUE DURING ELECTROPHYSIOLOGICAL MAPPING

CROSS-REFERENCE TO RELATED APPLICATIONS

This application claims the benefit of U.S. provisional application No. 62/466,079, filed 2 Mar. 2017, which is hereby incorporated by reference as though fully set forth herein.

BACKGROUND

The present disclosure relates generally to electrophysiological mapping, such as may be performed in cardiac diagnostic and therapeutic procedures. In particular, the present disclosure relates to systems, apparatuses, and methods for differentiating adipose tissue (that is, high fat content tissue) from scar tissue during electrophysiological mapping.

Epicardial mapping has become an important diagnostic tool for ablation of ventricular tachycardia ("VT") in the presence of structural cardiac arrhythmias. Ventricular arrhythmias can often be caused by scar tissue regions with low-voltage electrograms located on the ventricular epicardial surface of the heart. Therefore, voltage mapping is often used to identify regions of scar tissue.

Tissue with a high concentration of fat also exhibits low voltage markings. Thus, voltage mapping can erroneously detect adipose tissue as scar tissue.

BRIEF SUMMARY

Disclosed herein is a method of differentiating adipose tissue from scar tissue, including: collecting an electrophysiology data point, wherein the electrophysiology data point includes an electrophysiological signal associated with a tissue location, wherein the electrophysiological signal possesses one or more characteristics; and computing one or more of: an adipose tissue probability for the tissue location as a function of the one or more characteristics of the electrophysiological signal; and a scar tissue probability for the tissue location as a function of the one or more characteristics of the electrophysiological signal.

In embodiments of the disclosure, the adipose tissue probability for the tissue location is computed as a function of the one or more characteristics of the electrophysiological signal and one or more dielectric properties measured at the tissue location; and the scar tissue probability for the tissue location is computed as a function of the one or more characteristics of the electrophysiological signal and the one or more dielectric properties measured at the tissue location.

The one or more characteristics of the electrophysiological signal can be selected from the group consisting of signal duration, signal amplitude, signal fractionation, and late potentials. Likewise, the one or more dielectric properties measured at the tissue location can be selected from the group consisting of tissue impedance, tissue conductivity, and tissue permittivity.

The one or more dielectric properties measured at the tissue location can be measured using a first electrode on a first spline of a multi-electrode catheter and a second electrode on the first spline of the multi-electrode catheter (e.g., two electrodes on the same spline) and/or by a first electrode on a first spline of a multi-electrode catheter and a second electrode on a second spline of the multi-electrode catheter (e.g., two electrodes on two different splines).

Various probability functions are contemplated. By way of example only, the function of the one or more characteristics of the electrophysiological signal used to compute the scar tissue probability for the tissue location can more heavily weight the one or more characteristics of the electrophysiological signal associated with the tissue location than the one or more dielectric properties measured at the tissue location.

It is also within the scope of the disclosure to repeat the steps: collecting an electrophysiology data point, wherein the electrophysiology data point includes an electrophysiological signal associated with a tissue location, wherein the electrophysiological signal possesses one or more characteristics; and computing the adipose tissue probability and the scar tissue probability a plurality of times for a plurality of collected electrophysiology data points, thereby computing one or more of an adipose tissue probability map and a scar tissue probability map. A graphical representation of the one or more of the adipose tissue probability map and the scar tissue probability map can then be output on a three-dimensional tissue geometry model.

Also disclosed herein is a method of generating a tissue map that differentiates between adipose tissue and scar tissue from an electrophysiology map including a plurality of electrophysiology data points, each electrophysiology data point including an electrophysiological signal and one or more dielectric properties associated with a tissue location. The method includes: for each electrophysiology data point of the plurality of electrophysiology data points, computing one or more of: an adipose tissue probability for the tissue location as a function of the one or more characteristics of the electrophysiological signal and the one or more dielectric properties associated with the tissue location; and a scar tissue probability for the tissue location as a function of the one or more characteristics of the electrophysiological signal and the one or more dielectric properties associated with the tissue location; and generating one or more of an adipose tissue probability map and a scar tissue probability map. A graphical representation of the one or more of the adipose tissue probability map and the scar tissue probability map can be output on a three-dimensional tissue geometry model.

As described above, various probability functions are within the scope of the disclosure. For example, the function of the one or more characteristics of the electrophysiological signal and the one or more dielectric properties associated with the tissue location used to compute the adipose tissue probability for the tissue location can utilize a first set of user-preset weighting factors for the one or more characteristics of the electrophysiological signal and the one or more dielectric properties associated with the tissue location; and the function of the one or more characteristics of the electrophysiological signal and the one or more dielectric properties associated with the tissue location used to compute the scar tissue probability for the tissue location can utilize a second set of user-preset weighting factors for the one or more characteristics of the electrophysiological signal and the one or more dielectric properties associated with the tissue location. The first and/or second sets of user-preset weighting factors can be spatially-dependent (that is, their relative values can depend upon where mapping data is acquired).

The one or more characteristics of the electrophysiological signal can be selected from the group consisting of signal duration, signal amplitude, signal fractionation, and late potentials. Similarly, the one or more dielectric properties can be selected from the group consisting of tissue impedance, tissue conductivity, and tissue permittivity. As another example of a probability function within the scope of the instant disclosure, the function of the one or more characteristics of the electrophysiological signal and the one or more dielectric properties associated with the tissue location used to compute the scar tissue probability for the tissue location can more heavily weight signal fractionation than tissue impedance and more heavily weights tissue impedance than signal amplitude. For example, signal fractionation can be weighted twice as heavily tissue impedance.

In yet another embodiment, the instant disclosure provides a method of differentiating adipose tissue from scar tissue, including: processing an electrophysiological signal associated with a tissue location, wherein the electrophysiological signal possesses one or more characteristics, to compute: an adipose tissue probability for the tissue location as a function of the one or more characteristics of the electrophysiological signal; and a scar tissue probability for the tissue location as a function of the one or more characteristics of the electrophysiological signal. The one or more characteristics of the electrophysiological signal can be selected from the group consisting of signal duration, signal amplitude, signal fractionation, and late potentials.

It is also contemplated that the adipose tissue probability for the tissue location can be computed as a function of the one or more characteristics of the electrophysiological signal and one or more dielectric properties measured at the tissue location. Similarly, the scar tissue probability for the tissue location can be computed as a function of the one or more characteristics of the electrophysiological signal and the one or more dielectric properties measured at the tissue location. The one or more dielectric properties measured at the tissue location can be selected from the group consisting of tissue impedance, tissue conductivity, and tissue permittivity.

According to aspects of the disclosure, the step of processing an electrophysiological signal associated with a tissue location can be repeated a plurality of times. This allows for the generation of an adipose tissue probability map and a scar tissue probability map. A graphical representation of at least one of the adipose tissue probability map and the scar tissue probability map can be output on a three-dimensional tissue geometry model.

The instant disclosure also provides a system for differentiating adipose tissue from scar tissue, including a tissue probability determination processor configured to: receive as input an electrophysiology data point, wherein the electrophysiology data point includes an electrophysiological signal associated with a tissue location, wherein the electrophysiological signal possesses one or more characteristics; and compute one or more of an adipose tissue probability for the tissue location as a function of the one or more characteristics of the electrophysiological signal; and a scar tissue probability for the tissue location as a function of the one or more characteristics of the electrophysiological signal.

In embodiments of the disclosure, the tissue probability determination processor can further configured be to compute the adipose tissue probability for the tissue location as a function of the one or more characteristics of the electrophysiological signal and one or more dielectric properties measured at the tissue location; and compute the scar tissue probability for the tissue location as a function of the one or more characteristics of the electrophysiological signal and the one or more dielectric properties measured at the tissue location.

The one or more characteristics of the electrophysiological signal can be selected from the group consisting of signal duration, signal amplitude, signal fractionation, and late potentials. The one or more dielectric properties measured at the tissue location can be selected from the group consisting of tissue impedance, tissue conductivity, and tissue permittivity.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 5 depicts representative distributions of electrogram fractionation in adipose tissue and scar tissue, as measured by the number of deflections in the electrogram.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The present disclosure provides methods, apparatuses, and systems to aid in differentiating between structural tissue (e.g., veins), healthy tissue, scar tissue, and high fat content tissue (adipose tissue), in particular during electrophysiological mapping procedures. For purposes of illustration, several exemplary embodiments will be described in detail herein in the context of a ventricular mapping procedure carried out using an electrophysiology mapping system (e.g., using a electroanatomical mapping system such as the EnSite Precision™ cardiac mapping system from Abbott Laboratories). It is contemplated, however, that the methods, apparatuses, and systems described herein can be utilized in other contexts, including, but not limited to atrial mapping and/or coronary sinus mapping.

Figure 1:
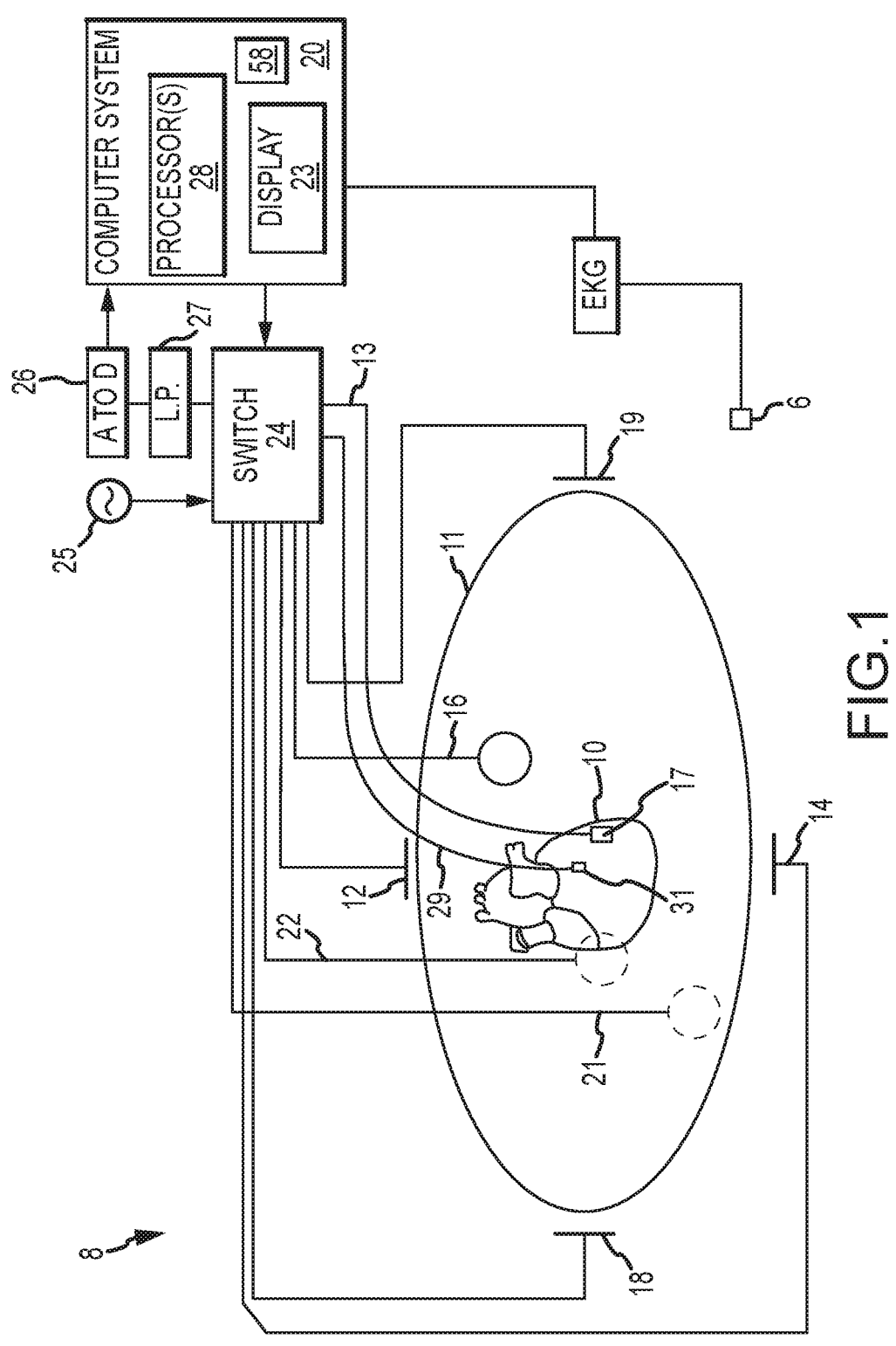
FIG. 1 is a schematic diagram of an exemplary electro-anatomical mapping system.

FIG. 1 shows a schematic diagram of an exemplary system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10. In some embodiments, and as discussed further herein, the system 8 can facilitate differentiation between scar tissue and adipose tissue, such as by computing (1) a probability that a particular tissue location is scar tissue and/or (2) a probability that the particular tissue location is adipose tissue.

As one of ordinary skill in the art will recognize, and as will be further described below, system 8 determines the location, and in some aspects the orientation, of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only a single lead 6 and its connection to computer 20 is illustrated in FIG. 1.

A representative catheter 13 having at least one electrode 17 is also shown. This representative catheter electrode 17 is referred to as the "roving electrode," "moving electrode," or "measurement electrode" throughout the specification. Typically, multiple electrodes 17 on catheter 13, or on multiple such catheters, will be used. In one embodiment, for example, the system 8 may comprise sixty-four electrodes on twelve catheters disposed within the heart and/or vasculature of the patient. Of course, this embodiment is merely exemplary, and any number of electrodes and catheters may be used.

Figure 2:
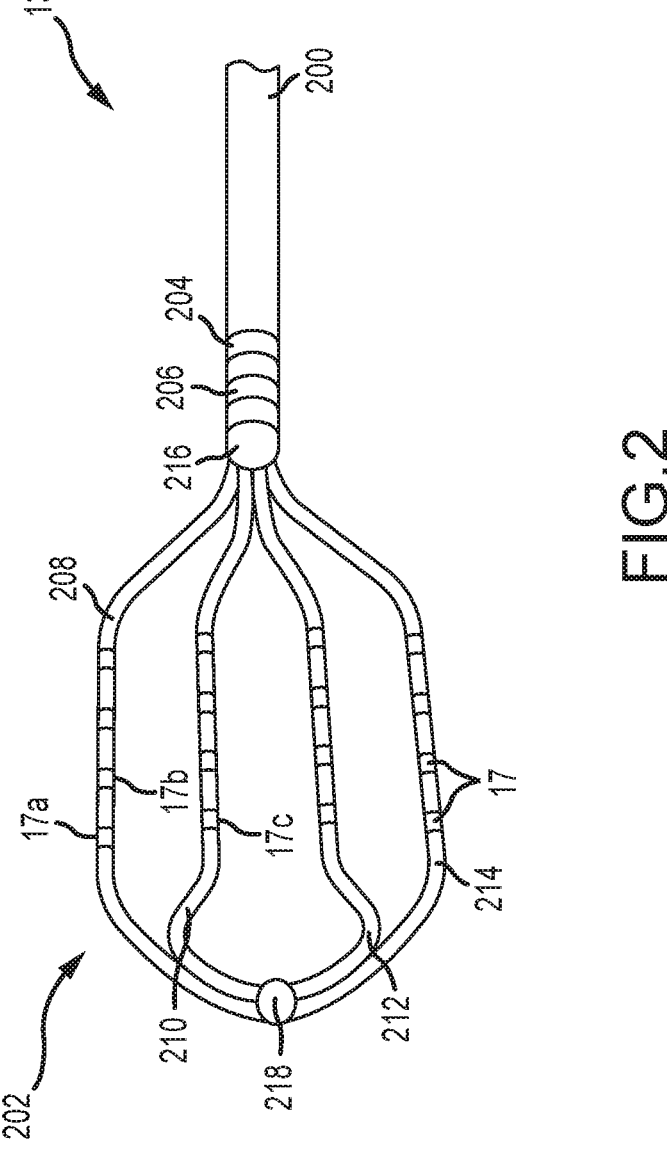
FIG. 2 depicts an exemplary catheter that can be used to differentiate adipose tissue from scar tissue according to aspects of the instant disclosure.

In particular, for purposes of this disclosure, a segment of an exemplary multi-electrode catheter 13, often referred to as a high density ("HD") grid catheter, is shown in FIG. 2. HD grid catheter 13 includes a catheter body 200 coupled to a paddle 202. Catheter body 200 can further include first and second body electrodes 204, 206, respectively. Paddle 202 can include a first spline 208, a second spline 210, a third spline 212, and a fourth spline 214, which are coupled to catheter body 200 by a proximal coupler 216 and to each other by a distal coupler 218. In one embodiment, first spline 208 and fourth spline 214 can be one continuous segment and second spline 210 and third spline 212 can be another continuous segment. In other embodiments, the various splines 208, 210, 212, 214 can be separate segments coupled to each other (e.g., by proximal and distal couplers 216, 218, respectively).

As described above, splines 208, 210, 212, 214 can include any number of electrodes 17; in FIG. 2, sixteen electrodes 17 are shown arranged in four-by-four array. It should also be understood that electrodes 17 can be evenly and/or unevenly spaced, as measured both along and between splines 208, 210, 212, 214.

Catheter 13 (or multiple such catheters) are typically introduced into the heart and/or vasculature of the patient via one or more introducers using familiar procedures. Indeed, various approaches to introduce catheter 13 into the left ventricle of the patient's heart 10, such as transseptal approaches, will be familiar to those of ordinary skill in the art, and therefore need not be further described herein.

Since each electrode 17 lies within the patient, location data may be collected simultaneously for each electrode 17 by system 8. Similarly, each electrode 17 can be used to gather electrophysiological data from the cardiac surface. The ordinarily skilled artisan will be familiar with various modalities for the acquisition and processing of electrophysiology data points (including, for example, both contact and non-contact electrophysiological mapping), such that further discussion thereof is not necessary to the understanding of the techniques disclosed herein. Likewise, various techniques familiar in the art can be used to generate a graphical representation from the plurality of electrophysiology data points. Insofar as the ordinarily skilled artisan will appreciate how to create electrophysiology maps from electrophysiology data points, the aspects thereof will only be described herein to the extent necessary to understand the instant disclosure.

Returning now to FIG. 1, in some embodiments, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three)

instances of signal generator 25 may be provided, one for each measurement axis (that is, each surface electrode pairing).

The computer 20 may comprise, for example, a conventional general-purpose computer, a special-purpose computer, a distributed computer, or any other type of computer. The computer 20 may comprise one or more processors 28, such as a single central processing unit ("CPU"), or a plurality of processing units, commonly referred to as a parallel processing environment, which may execute instructions to practice the various aspects described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17 placed in the heart 10 are exposed to the field from a current pulse and are measured with respect to ground, such as belly patch 21. In practice the catheters within the heart 10 may contain more or fewer electrodes than the sixteen shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which system 8 measures positions. Data sets from each of the surface electrodes, the internal electrodes, and the virtual electrodes may all be used to determine the location of the roving electrodes 17 within heart 10.

The measured voltages may be used by system 8 to determine the location in three-dimensional space of the electrodes inside the heart, such as roving electrodes 17 relative to a reference location, such as reference electrode 31. That is, the voltages measured at reference electrode 31 may be used to define the origin of a coordinate system, while the voltages measured at roving electrodes 17 may be used to express the location of roving electrodes 17 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described, for example, in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ cardiac mapping and visualization system of Abbott Laboratories, which generates electrical fields as described above, or another localization system that relies upon electrical fields. Other localization systems, however, may be used in connection with the present teachings, including for example, systems that utilize magnetic fields instead of or in addition to electrical fields for localization. Examples of such systems include, without limitation, the CARTO navigation and location system of Biosense Webster, Inc., the AURORA® system of Northern Digital Inc., Sterotaxis' NIOBE® Magnetic Navigation System, as well as Medi-Guide™ Technology and the EnSite™ Precision™ system, both from Abbott Laboratories.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

Aspects of the disclosure relate to differentiating between scar tissue and adipose tissue during electrophysiological mapping. The system 8 can therefore also include a tissue differentiation module 58 that can be used to determine (1) the probability that a given tissue location is scar tissue and/or (2) the probability that a given tissue location is adipose tissue.

As described above, the teachings herein can be applied to good advantage in the ventricular electrophysiological mapping. Those of ordinary skill in the art will appreciate that electrophysiology maps include a plurality of electrophysiology data points, and that each electrophysiology data point in turn includes both measured electrophysiology data (e.g., an electrophysiological signal, such as a cardiac electrogram ("EGM")) and location data (e.g., information regarding the location of catheter 13 and/or electrodes 17 thereon), thus allowing the measured electrophysiology information to be associated with a particular location in space (that is, allowing the measured electrophysiology information to be interpreted as indicative of electrical activity at a particular tissue location). According to embodiments of the disclosure, electrophysiology data points can also include information about dielectric properties, such as permittivity, conductivity, and impedance, of the tissue location.

Figure 3:
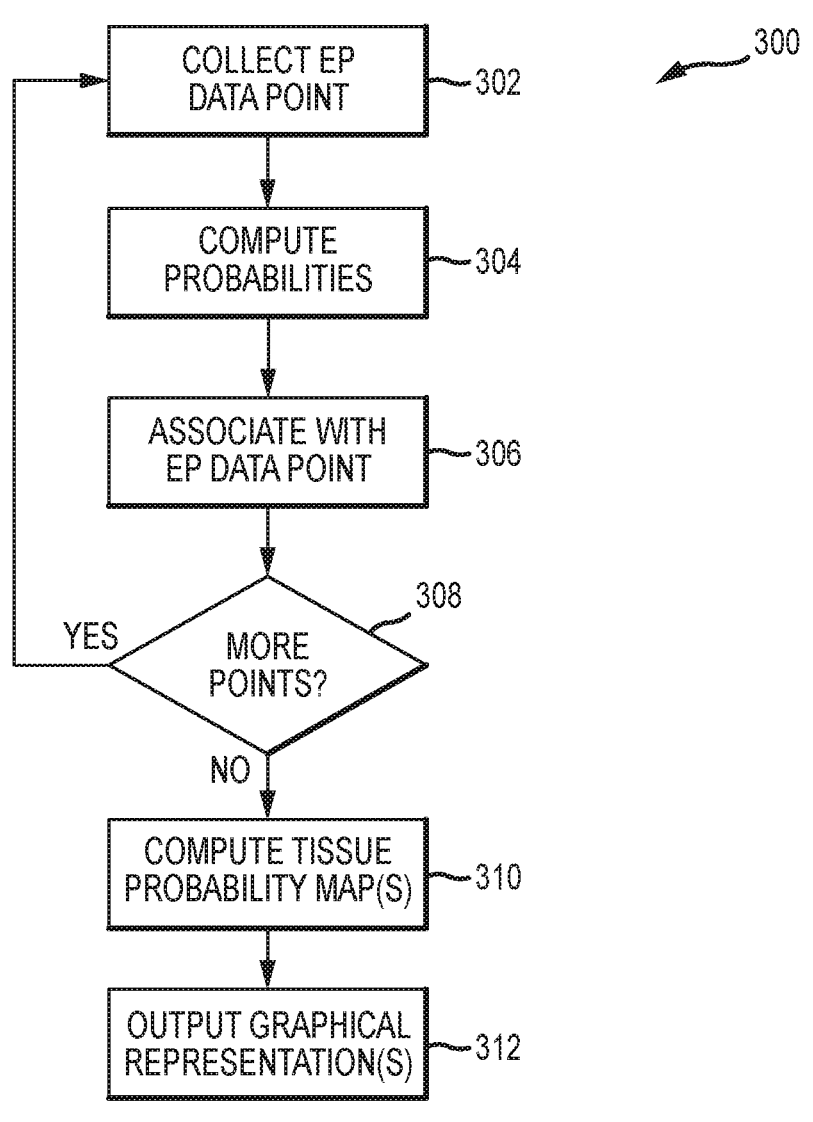
FIG. 3 is a flowchart of representative steps that can be followed according to exemplary embodiments disclosed herein.

One exemplary method for differentiating adipose tissue from scar tissue in connection with electrophysiological mapping according to the present teachings will be explained with reference to the flowchart 300 of representative steps presented as FIG. 3. In some embodiments, for example, flowchart 300 may represent several exemplary steps that can be carried out by the computer 20 of FIG. 1 (e.g., by processor 28, including tissue differentiation module 58). It should be understood that the representative steps described below can be either hardware- or software-implemented. For the sake of explanation, the term "signal processor" is used herein to describe both hardware- and software-based implementations of the teachings herein.

An electrophysiology data point is collected in block 302. As described above, the collected electrophysiology data point includes an electrophysiological signal (e.g., an EGM signal) associated with a tissue location, and can optionally further include dielectric properties of the tissue location.

The electrophysiological signal (e.g., the EGM signal) possesses one or more characteristics that can be analyzed according to aspects of the instant disclosure to compute scar tissue and/or adipose tissue probabilities as described below. Suitable signal characteristics for analysis include, without limitation, signal duration, signal amplitude, signal fractionation, and late potentials. Each of these is discussed in detail below.

Figure 4:
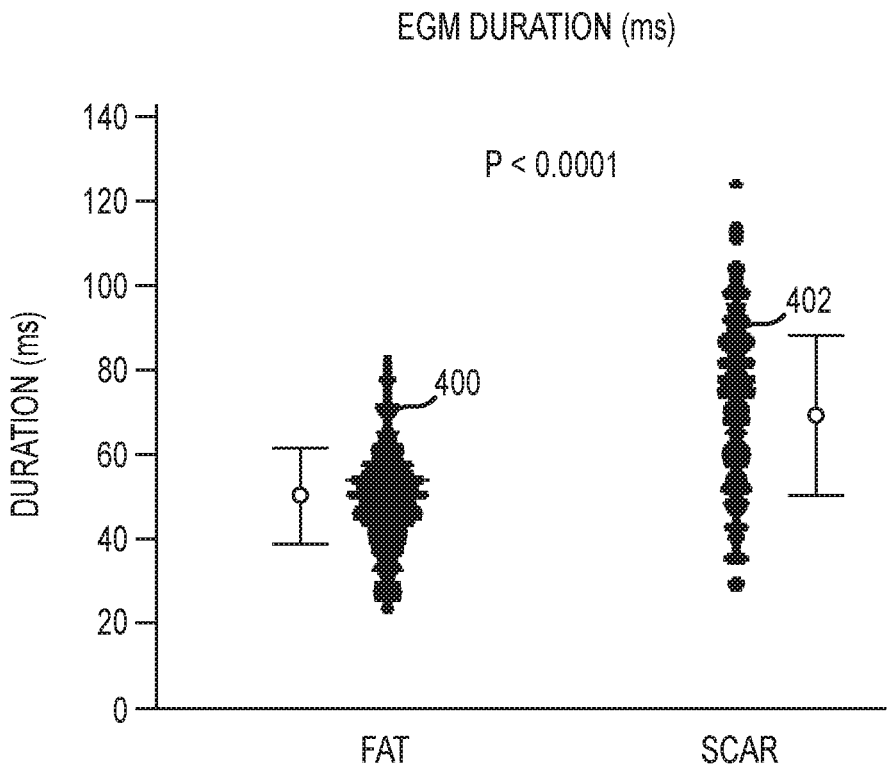
FIG. 4 depicts representative distributions of electrogram durations in adipose tissue and scar tissue.

Signal Duration. Scar tissue generally exhibits longer-duration EGMs than adipose tissue. For example, FIG. 4, which appears in Tung et al., "Distinguishing epicardial fat from scar: Analysis of electrograms using high-density electroanatomic mapping in a novel porcine infarct model," Heart Rhythm 2010; 7:389-395, plots the distribution of EGM duration for adipose tissue 400 and for scar tissue 402. As shown in FIG. 4, adipose tissue EGM duration (distribution 400) is about 50.1 ms±11.6 ms, and scar tissue EGM duration (distribution 402) is about 68.6 ms±18.9 ms. EGM duration from healthy myocardial tissue typically ranges from about 50.0 ms±6.7 ms. A cutoff point of 80 ms has a 99% specificity for scar tissue.

Signal Amplitude. Low amplitude signals are typically characteristic of adipose and scar tissue EGMs. Mean bipolar EGM amplitudes are typically low for adipose tissue (about 0.77 mV±0.34 mv) and for scar tissue (about 0.75 my±0.38 mV) by comparison to healthy myocardial tissue (about 5.9 mV±3.5 mV).

Figure 5:
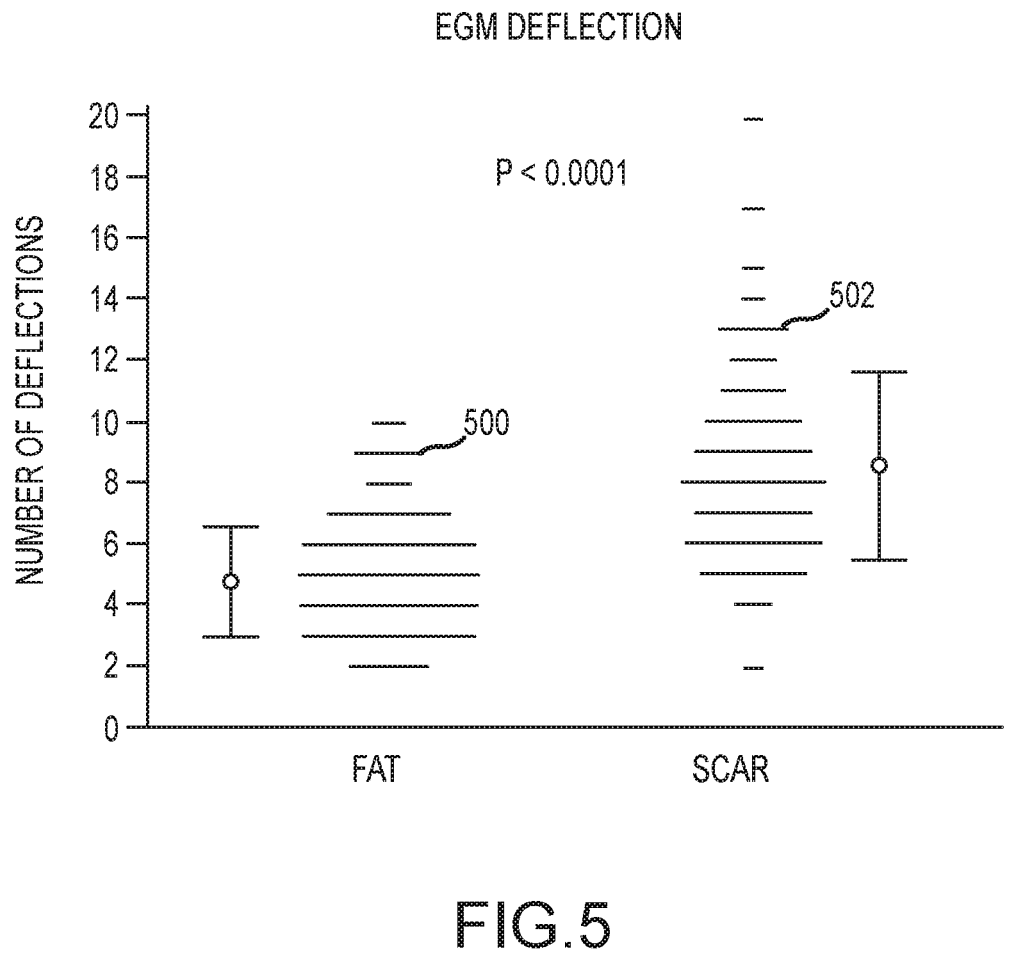

Signal Fractionation. Scar tissue EGMs typically present greater fractionation than adipose tissue EGMs, such as measured by the number of deflections in the EGM. For example, FIG. 5, which also appears in Tung et al., supra, plots the distribution of the number of deflections in adipose tissue 500 and for scar tissue 502. As shown in FIG. 5, adipose tissue EGMs (distribution 500) exhibit about 4.7±1.8 deflections, while scar tissue EGMs (distribution 502) exhibit about 8.5±3.1 deflections.

Late Potentials. Late potentials are rarely present in adipose tissue EGMs. Late potentials are present in about 39.1% of scar tissue EGMs. The presence of late potentials in an EGM has a specificity of about 99% for scar tissue.

As described above, the collected electrophysiology data point can optionally include one or more dielectric properties measured at the tissue location. These properties can also be analyzed when computing adipose and/or scar tissue probabilities according to the instant teachings. Suitable dielectric properties for such analysis include, without limitation, tissue impedance, tissue conductivity, and tissue permittivity.

The dielectric properties can be measured between electrodes on a single spline (e.g., between electrodes 17a and 17b in FIG. 2) and/or between electrodes across splines (e.g., between electrodes 17a and 17c in FIG. 2).

Figure 6:
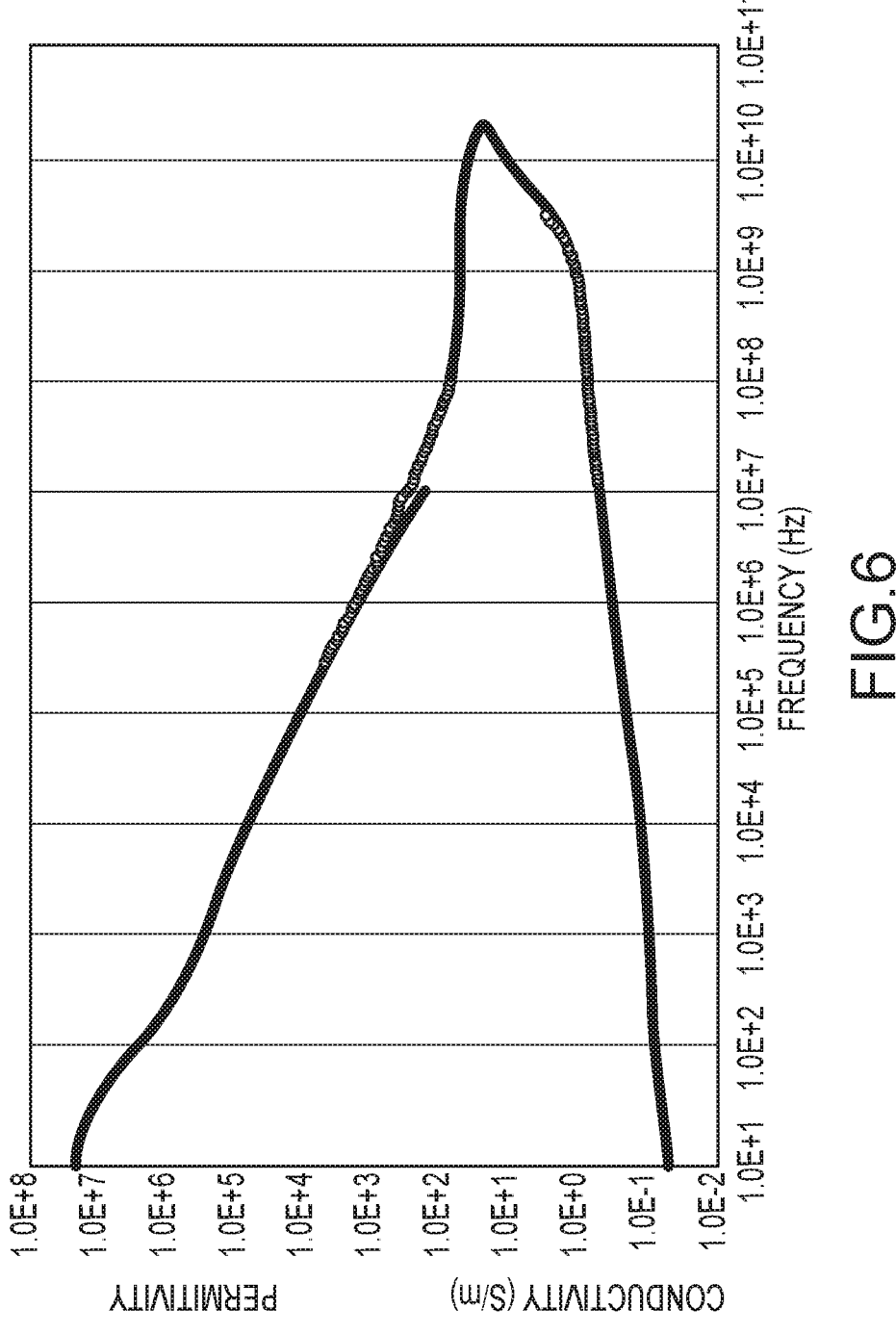
FIG. 6 contains illustrative plots of tissue permittivity and tissue conductivity over a range of frequencies for healthy cardiac muscle.
Figure 7:
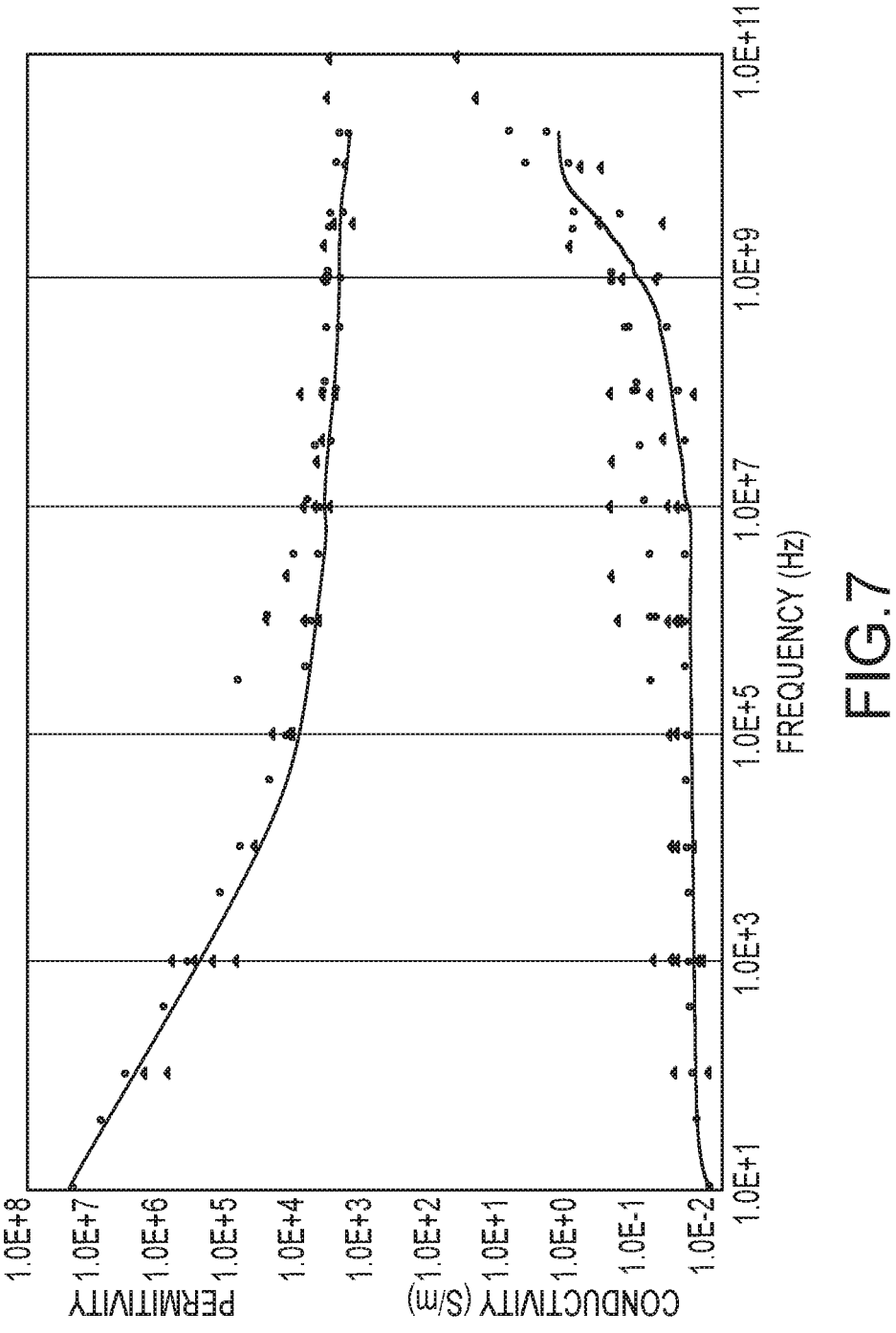
FIG. 7 contains illustrative plots of tissue permittivity and tissue conductivity over a range of frequencies for adipose tissue.

FIG. 6 depicts the relationships between tissue permittivity and tissue conductivity at various stimulation frequencies for healthy cardiac muscle. FIG. 7 depicts the same relationships for adipose tissue. When stimulated at the same frequency, FIGS. 6 and 7 illustrate that cardiac muscle and adipose tissue exhibit different combinations of tissue permittivity and conductivity, which differences can be used to distinguish between tissue types according to the teachings herein. FIGS. 6 and 7 appear in Gabriel et al., "The dielectric properties of biological tissues: II. Measurements in the frequency range 10 Hz to 20 GhZ," Phys. Med. Biol. 41, 1996, 2251-2269.

In block 304, one or more of an adipose tissue probability and a scar tissue probability are computed. As used herein, the term "adipose tissue probability" refers to the probability that the tissue location of the collected electrophysiology data point is adipose tissue. Similarly, the term "scar tissue probability" is used herein to refer to the probability that the tissue location of the collected electrophysiology data point is scar tissue.

According to aspects of the disclosure, for a given electrophysiology data point, the adipose tissue probability and the scar tissue probability are independent. That is, it is not required that, for a given electrophysiology data point, the sum of the adipose tissue probability and the scar tissue probability must equal 1.0.

It is contemplated that both the adipose tissue probability and the scar tissue probability will be computed as functions of one or more characteristics of the electrophysiological signal and/or one or more dielectric properties of the tissue location. More particularly, it is contemplated that the adipose tissue probability and the scar tissue probability will be computed as weighted functions of one or more characteristic of the electrophysiological signal and/or one or more dielectric properties of the tissue location.

For example, one suitable definition for the scar tissue probability is $$p_{scar} = a_{xyz}(\text{amplitude}) + b_{xyz}(\text{fractionation}) + c_{xyz}(\text{impedance}) + d_{xyz}(\text{late potentials})$$

where amplitude is the amplitude of the electrophysiological signal; fractionation is a measure of the fractionation of the electrophysiological signal (e.g., the number of deflections in the EGM), impedance is the tissue impedance between electrodes 17 on catheter 13, and late potentials reflects the presence of late potentials in the signal. $a_{xyz}$, $b_{xyz}$, $c_{xyz}$, and $d_{xyz}$ are weight factors that are spatially-dependent (e.g., their relative values depend upon where mapping data is acquired). For example, amplitude may have a lower weight than fractionation or impedance when mapping in the coronary sinus ridge. In one embodiment, $a_{xyz}$ equals 0.1, $b_{xyz}$ equals 0.6, $c_{xyz}$ equals 0.3, and $d_{xyz}$ equals 0.0.

An equation of similar form can be used to compute adipose tissue probability, though the relative weights may differ when computing the adipose tissue probability instead of the scar tissue probability:

$$p_{adipose} = e_{xyz}(\text{amplitude}) + f_{xyz}(\text{fractionation}) + g_{xyz}(\text{impedance}) + h_{xyz}(\text{late potentials})$$

where amplitude is the amplitude of the electrophysiological signal; fractionation is a measure of the fractionation of the electrophysiological signal (e.g., the number of deflections in the EGM), impedance is the tissue impedance between electrodes 17 on catheter 13, and late potentials reflects the presence of late potentials in the signal. $e_{xyz}$, $f_{xyz}$, $g_{xyz}$, and $h_{xyz}$ are weight factors that are spatially-dependent (e.g., their relative values depend upon where mapping data is acquired). For example, amplitude may have a higher weight than fractionation or impedance when mapping in the coronary sinus ridge. In one embodiment, $e_{xyz}$ equals 0.2, $f_{xyz}$ equals 0.2, $g_{xyz}$ equals 0.4, and $h_{xyz}$ equals 0.2.

In one embodiment, It is contemplated that the variables utilized in the probability functions (e.g., the characteristics of the electrophysiological signal and the dielectric properties) can be user-selected. It is further contemplated that the weighting factors assigned to these user-selected variables can be user-preset (that is, user-defined and -adjusted). By adjusting the variables and/or weighting factors, the practitioner can manipulate the sensitivity and/or specificity of the probability calculations depending upon, for example, the particular substrate being mapped. Of course, it is also within the scope of the instant disclosure for the variables utilized in the probability functions and/or their relative weights may be pre-selected depending, for example, upon the type of electrophysiology study being conducted.

Once computed, the adipose and/or scar tissue probabilities can be associated with the collected electrophysiology data point in block 306.

Decision block 308 checks to see if additional electrophysiology data points remain to be processed. In this regard, it should be understood that the teachings herein can be applied in real time (e.g., electrophysiology data points can be analyzed for scar tissue and/or adipose tissue probabilities at the time they are collected) or during postprocessing (e.g., electrophysiology data points making up an electrophysiology map can be analyzed for scar tissue and/or adipose tissue probabilities after they have been collected). If there are additional electrophysiology data points to process ("YES" exit from block 308), for example because the practitioner wishes to collect additional data points or because a received electrophysiology map contains additional electrophysiology data points, the process can return to block 302 to collect and analyze an additional electrophysiology data point.

In general, however, once all electrophysiology data points have been analyzed ("NO" exit from block 308), one or more tissue probability maps can be computed in block 310 from the plurality of adipose and/or scar tissue probabilities computed in block 304. More particularly, block 310 can include the computation of a scar tissue probability map, which describes the probability that tissue locations over a given tissue region are scar tissue, and/or an adipose tissue probability map, which describes the probability that tissue locations over a given tissue region have a high fat concentration.

Graphical representations of the tissue probability maps can be output in block 312, for example by displaying the computed probabilities numerically and/or in colorscale or greyscale on a three-dimensional tissue geometry model (e.g., a three-dimensional cardiac geometry model generated by system 8; a CT or MRI cardiac image; or the like). Such representations can aid a practitioner in differentiating between scar tissue and adipose tissue on the ventricular epicardial surface, which can help guide the practitioner in delivering ablation therapy in the treatment of VT.

Although several embodiments have been described above with a certain degree of particularity, those skilled in the art could make numerous alterations to the disclosed embodiments without departing from the spirit or scope of this invention.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of differentiating adipose tissue from scar tissue, comprising:

collecting a plurality of electrophysiology data points, wherein each electrophysiology data point of the plurality of electrophysiology data points includes an electrophysiological signal associated with a tissue location, wherein the electrophysiological signal possesses one or more morphological characteristics;

for each electrophysiology data point of the plurality of electrophysiology data points, computing one or more of:

an adipose tissue probability for the respective tissue location as a first function of the one or more morphological characteristics of the respective electrophysiological signal, wherein the first function utilizes a first set of spatially-dependent weighting factors for the one or more morphological characteristics of the respective electrophysiological signal, thereby computing an adipose tissue probability map; and a scar tissue probability for the respective tissue location as a second function of the one or more morphological characteristics of the respective electrophysiological signal, wherein the second function utilizes a second set of spatially-dependent weighting factors for the one or more morphological characteristics of the respective electrophysiological signal, thereby computing a scar tissue probability map;

outputting a graphical representation of at least one of the adipose tissue probability map and the scar tissue probability map on a three-dimensional tissue geometry model; and further comprising delivering ablation therapy to a scar tissue based upon the scar tissue probability map.

2. The method according to claim 1, wherein:

the adipose tissue probability for the respective tissue location is computed as a first function of the one or more morphological characteristics of the respective electrophysiological signal and one or more dielectric properties measured at the respective tissue location; and the scar tissue probability for the respective tissue location is computed as a second function of the one or more morphological characteristics of the respective electrophysiological signal and the one or more dielectric properties measured at the respective tissue location.

3. The method according to claim 2, wherein the one or more morphological characteristics of the respective electrophysiological signal are selected from the group consisting of signal duration, signal amplitude, signal fractionation, and late potentials.

4. The method according to claim 2, wherein the one or more dielectric properties measured at the respective tissue location are selected from the group consisting of tissue impedance, tissue conductivity, and tissue permittivity.

5. The method according to claim 2, wherein the one or more dielectric properties measured at the respective tissue location are measured using a first electrode on a first spline of a multi-electrode catheter and a second electrode on the first spline of the multi-electrode catheter.

6. The method according to claim 2, wherein the one or more dielectric properties measured at the respective tissue location are measured using a first electrode on a first spline of a multi-electrode catheter and a second electrode on a second spline of the multi-electrode catheter.

7. The method according to claim 2, wherein the second function of the one or more morphological characteristics of the respective electrophysiological signal and the one or more dielectric properties measured at the respective tissue location more heavily weights the one or more morphological characteristics of the respective electrophysiological signal than the one or more dielectric properties measured at the respective tissue location.

\* \* \* \* \*